US012748023B2

(12) United States Patent
Kernozicky et al.

(10) Patent No.: US 12,748,023 B2
(45) Date of Patent: Sep. 29, 2026

(54) LOCALIZED REWORK USING POWDER BED FUSION GENERATED SEGMENTS

(71) Applicant: RTX Corporation, Farmington, CT (US)

(72) Inventors: Garrett Kernozicky, Mansfield, CT (US); Jesse R. Boyer, Middletown, CT (US); Ashwin Raghavan, Shrewsbury, MA (US); Peter John Breitzmann, Aldie, VA (US); Praba Kharan Baptist, Glastonbury, CT (US); Michael L. Vukovinsky, Chester, CT (US); Lawrence A Binek, Glastonbury, CT (US)

(73) Assignee: RTX Corporation, Farmington, CT (US)

( * ) Notice: Subject to any disclaimer, the term of this patent is extended or adjusted under 35 U.S.C. 154(b) by 240 days.

(21) Appl. No.: 18/352,945

(22) Filed: Jul. 14, 2023

(65) Prior Publication Data

US 2025/0020558 A1 Jan. 16, 2025

(51) Int. Cl.
*G01N 3/02* (2006.01)
*A61B 5/00* (2006.01)
(Continued)

(52) U.S. Cl.
CPC ............ *G01N 3/02* (2013.01); *A61B 5/4528* (2013.01); *G01B 5/30* (2013.01); *G01B 7/16* (2013.01); *G01M 5/0041* (2013.01)

(58) Field of Classification Search
CPC .. G01N 3/02; G01B 5/30; G01B 7/16; A61M 5/0041; G01M 5/0041; A61B 5/4528
(Continued)

(56) References Cited

U.S. PATENT DOCUMENTS 4,141,124 A * 2/1979 Ryan ........................ B23P 6/005 29/889.1
5,269,057 A * 12/1993 Mendham ............... F01D 5/005 29/402.13
(Continued)

FOREIGN PATENT DOCUMENTS

CN 104674210 6/2015
DE 102017115255 A1 * 1/2018 ............. F01D 5/186
(Continued)

OTHER PUBLICATIONS

USPTO; Advisory Action dated Oct. 7, 2024 in U.S. Appl. No. 18/352,984.
(Continued)

*Primary Examiner* — Stephanie E Bloss
*Assistant Examiner* — Kevin C Butler
(74) *Attorney, Agent, or Firm* — SNELL & WILMER L.L.P.

(57) ABSTRACT

A method for repairing a stator stage is disclosed herein. The method includes receiving a stator stage including a plurality of stator vanes disposed between an outer diameter and an inner diameter, analyzing the stator stage for defects, determining there is a first defect in a first segment of a the stator stage, the first segment including at least one of a first portion of the outer diameter, a first portion of the inner diameter, or a first stator vane, removing the first segment from the stator stage forming a void in the stator stage, manufacturing a second segment that is the same size as the first segment, attaching the second segment to the stator stage to fill the void, performing a blending process on the stator stage including the second segment to smooth the plurality of stator vanes including the second stator vane.

20 Claims, 8 Drawing Sheets

(51) Int. Cl.
*G01B 5/30* (2006.01)
*G01B 7/16* (2006.01)
*G01M 5/00* (2006.01)

(58) Field of Classification Search
USPC .......................................................... 73/760
See application file for complete search history.

(56) References Cited

U.S. PATENT DOCUMENTS

| | | | | |
|---|---|---|---|---|
| 5,779,437 | A | 7/1998 | Abdel-Messeh et al. | |
| 6,238,187 | B1 * | 5/2001 | Dulaney | B23P 6/005 416/223 R |
| 6,508,000 | B2 | 1/2003 | Burke et al. | |
| 6,568,077 | B1 | 5/2003 | Hellemann et al. | |
| 9,011,082 | B2 * | 4/2015 | Jones | F02K 1/822 415/127 |
| 9,434,031 | B2 * | 9/2016 | Feigleson | B23P 15/04 |
| 9,770,758 | B2 | 9/2017 | Xu | |
| 10,016,846 | B2 | 7/2018 | Krause | |
| 10,569,361 | B2 | 2/2020 | Lin | |
| 10,954,822 | B2 | 3/2021 | Innocenti et al. | |
| 11,224,915 | B2 | 1/2022 | Srinivasan et al. | |
| 11,325,211 | B2 * | 5/2022 | Maritano | B23K 26/14 |
| 11,712,738 | B2 * | 8/2023 | Ozbaysal | B22F 1/09 75/255 |
| 12,253,003 | B1 * | 3/2025 | Binek | F01D 9/044 |
| 2003/0095250 | A1 | 5/2003 | Kitagawa et al. | |
| 2007/0020093 | A1 * | 1/2007 | Giaimo | F01D 9/042 415/160 |
| 2007/0113402 | A1 | 5/2007 | Lutz et al. | |
| 2011/0099810 | A1 * | 5/2011 | Stankowski | F01D 5/005 29/888 |
| 2013/0164117 | A1 * | 6/2013 | Jones | F01D 17/141 415/127 |
| 2013/0189092 | A1 * | 7/2013 | Dube | F01D 11/001 415/200 |
| 2014/0082940 | A1 * | 3/2014 | Feigleson | F01D 9/04 29/889.22 |
| 2014/0184215 | A1 | 7/2014 | Nishimizu et al. | |
| 2016/0032743 | A1 * | 2/2016 | Duchaine | B29C 65/48 156/60 |
| 2016/0084094 | A1 * | 3/2016 | Feigleson | B23P 15/04 29/889.22 |
| 2017/0370220 | A1 * | 12/2017 | Morris | F04D 29/542 |
| 2018/0002039 | A1 * | 1/2018 | Finn | G06Q 10/20 |
| 2018/0010457 | A1 * | 1/2018 | Chabane | F01D 5/005 |
| 2019/0383161 | A1 | 12/2019 | Graham et al. | |
| 2020/0346310 | A1 | 11/2020 | Huttner et al. | |
| 2022/0234101 | A1 * | 7/2022 | Ozbaysal | B22F 5/009 |
| 2022/0268170 | A1 | 8/2022 | Andalam et al. | |
| 2023/0315948 | A1 * | 10/2023 | Roberts | F01D 5/34 703/1 |
| 2023/0347457 | A1 * | 11/2023 | Anders | F01D 5/005 |
| 2025/0020062 | A1 * | 1/2025 | Kernozicky | F01D 5/005 |

FOREIGN PATENT DOCUMENTS

| | | | | | |
|---|---|---|---|---|---|
| EP | 0882545 | | | 12/1998 | |
| EP | 0882545 | A3 | * | 12/1998 | B23P 6/00 |
| EP | 3670928 | A1 | * | 6/2020 | F01D 25/005 |
| EP | 2620591 | B1 | * | 3/2021 | F01D 11/001 |
| EP | 3670928 | B1 | * | 8/2022 | F01D 5/282 |
| EP | 4141124 | A1 | * | 3/2023 | C12N 9/0069 |
| EP | 4491849 | A1 | * | 1/2025 | B22F 5/04 |
| KR | 20230169176 | A | * | 12/2023 | B23Q 3/063 |
| WO | 2019212533 | | | 11/2019 | |

OTHER PUBLICATIONS

European Patent Office, European Search Report dated May 13, 2025 in Application No. 24186383.6.
USPTO; Final Office Action dated May 30, 2025 in U.S. Appl. No. 18/352,984.
USPTO; Final Office Action dated Jul. 30, 2024 in U.S. Appl. No. 18/352,984.
European Patent Office, European Search Report dated Dec. 9, 2024 in Application No. 2418824188005.3.
USPTO; Non-Final Office Action dated Dec. 27, 2024 in U.S. Appl. No. 18/352,984.
European Patent Office, Partial European Search Report dated Feb. 20, 2025 in Application No. 24186383.6.
USPTO; Non-Final Office Action dated Mar. 21, 2024 in U.S. Appl. No. 18/352,984.
USPTO; Advisory Action dated Aug. 7, 2025 in U.S. Appl. No. 18/352,984.
USPTO; Non-Final Office Action dated Jan. 9, 2026 in U.S. Appl. No. 18/352,984.
USPTO; Final Office Action dated May 29, 2026 in U.S. Appl. No. 18/352,984.

* cited by examiner

LOCALIZED REWORK USING POWDER BED FUSION GENERATED SEGMENTS

FIELD

The present disclosure generally relates turbine engine components, and more particularly, to rework systems and methods the turbine engine components.

BACKGROUND

Components, such as those used in turbine engines, may include defects or damage from either production of the component or from service use. Local rework to address these defects and/or damage to the components is generally a time and labor intensive process. Defects may be removed from the components and repair using a manual tungsten inert gas (TIG) weld process. This frequently results in excessive distortion of the components from the heat input nature of manual weld processing.

SUMMARY

A method for repairing defects in a stator stage is disclosed herein. The method includes receiving a stator stage including a plurality of stator vanes disposed between an outer diameter and an inner diameter, analyzing the stator stage for defects, determining, based on the analysis, that there is a first defect in a first segment of a the stator stage, the first segment including at least one of a first portion of the outer diameter, a first portion of the inner diameter, or a first stator vane, removing the first segment from the stator stage forming a void in the stator stage, manufacturing a second segment including at least one of a second portion of the outer diameter, a second portion of the inner diameter, or a second stator vane, the second segment being the same size as the first segment, attaching the second segment to the stator stage to fill the void, performing a blending process on the stator stage including the second segment to smooth the plurality of stator vanes including the second stator vane.

In various embodiments, the analysis identifies defects on a surface of the stator stage and below the surface of the stator stage. In various embodiments, the analysis further includes using a heat map to identify locations of the stator stage with a higher probability of having a defect. In various embodiments, the first defect is disposed between a leading edge of the first stator vane and a trailing edge of the first stator vane, is disposed on the first portion of the outer diameter, or is disposed on the first portion of the inner diameter. In various embodiments, wherein the first segment has a first size and shape and the second segment has the first size and shape.

In various embodiments, the void is defined a first edge of the outer diameter and a second edge of the outer diameter and a first edge of the inner diameter and a second edge of the inner diameter. In various embodiments, the attaching the second segment includes attaching the first edge of the outer diameter and the second edge of the outer diameter to the second portion of the outer diameter and attaching the first edge of the inner diameter and the second edge of the inner diameter to the second portion of the inner diameter. In various embodiments, the first segment further includes a third stator vane adjacent the first stator vane. In various embodiments, the manufacturing the second segment includes using an additive manufacturing process. In various embodiments, the additive manufacturing process is a powder bed fusion process.

Also disclosed herein is a method of repairing a stator stage for use with a turbine engine. The method includes receiving the stator stage including a plurality of stator vanes disposed between an outer diameter and an inner diameter, the stator stage having a first defect identified on a first segment of the stator stage, the first segment including a first portion of the outer diameter, a first portion of the inner diameter, and a first stator vane, removing the first segment from the stator stage forming a void in the stator stage, the void defined by a first edge of the outer diameter and an opposing second edge of the outer diameter and a first edge of the inner diameter and an opposing second edge of the inner diameter, manufacturing a second segment including a second portion of a second outer diameter, a second portion of a second inner diameter, and a second stator vane, and attaching the second segment to the stator stage to fill the void, including attaching the second portion of the second outer diameter to the first edge of the outer diameter and the second edge of the outer diameter and attaching the second portion of the second inner diameter to the first edge of the inner diameter and the second edge of the inner diameter.

In various embodiments, the method of repairing the stator stage for use with the turbine engine further includes performing a blending process on the stator stage to smooth and shape the plurality of stator vanes, including the second stator vane of the second segment. In various embodiments, the method of repairing the stator stage for use with the turbine engine further includes forming a first edge profile on the first edge of the outer diameter and the opposing second edge of the outer diameter, forming a second edge profile on the first edge of the inner diameter and the opposing second edge of the inner diameter, forming a third edge profile on the second portion of the second outer diameter of the second segment, the third edge profile complimenting the first edge profile, and forming a fourth edge profile on the second portion of the second inner diameter of the second segment, the fourth edge profile complimenting the second edge profile.

In various embodiments, the first segment and the second segment have the same size and shape. In various embodiments, the size and shape of the first segment and the second segment are predefined. In various embodiments, the manufacturing the second segment including using a powder bed fusion process.

Also disclosed herein is a method of repairing a stator stage for use with a turbine engine. The method includes receiving the stator stage including a plurality of stator vanes and a void, the plurality of stator vanes being disposed between a first outer diameter and first inner diameter and the void being defined by a first edge of the first outer diameter and an opposing second edge of the first outer diameter and a first edge of the first inner diameter and an opposing second edge of the first inner diameter, manufacturing a first segment including a first portion of a second outer diameter, a first portion of a second inner diameter, and a first stator vane, and attaching the first segment to the stator stage to fill the void, including attaching the first portion of the second outer diameter to the first edge of the first outer diameter and the opposing second edge of the first outer diameter, and attaching the first portion of the second inner diameter to the first edge of the first inner diameter and the opposing second edge of the first inner diameter.

In various embodiments, the void has a predefined size and shape and the first segment is manufactured to match the predefined size and shape. In various embodiments, the manufacturing the first segment includes using a powder bed fusion process. In various embodiments, the manufacturing the first segment includes forming an edge profile on the first portion of the second outer diameter.

The foregoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1A:
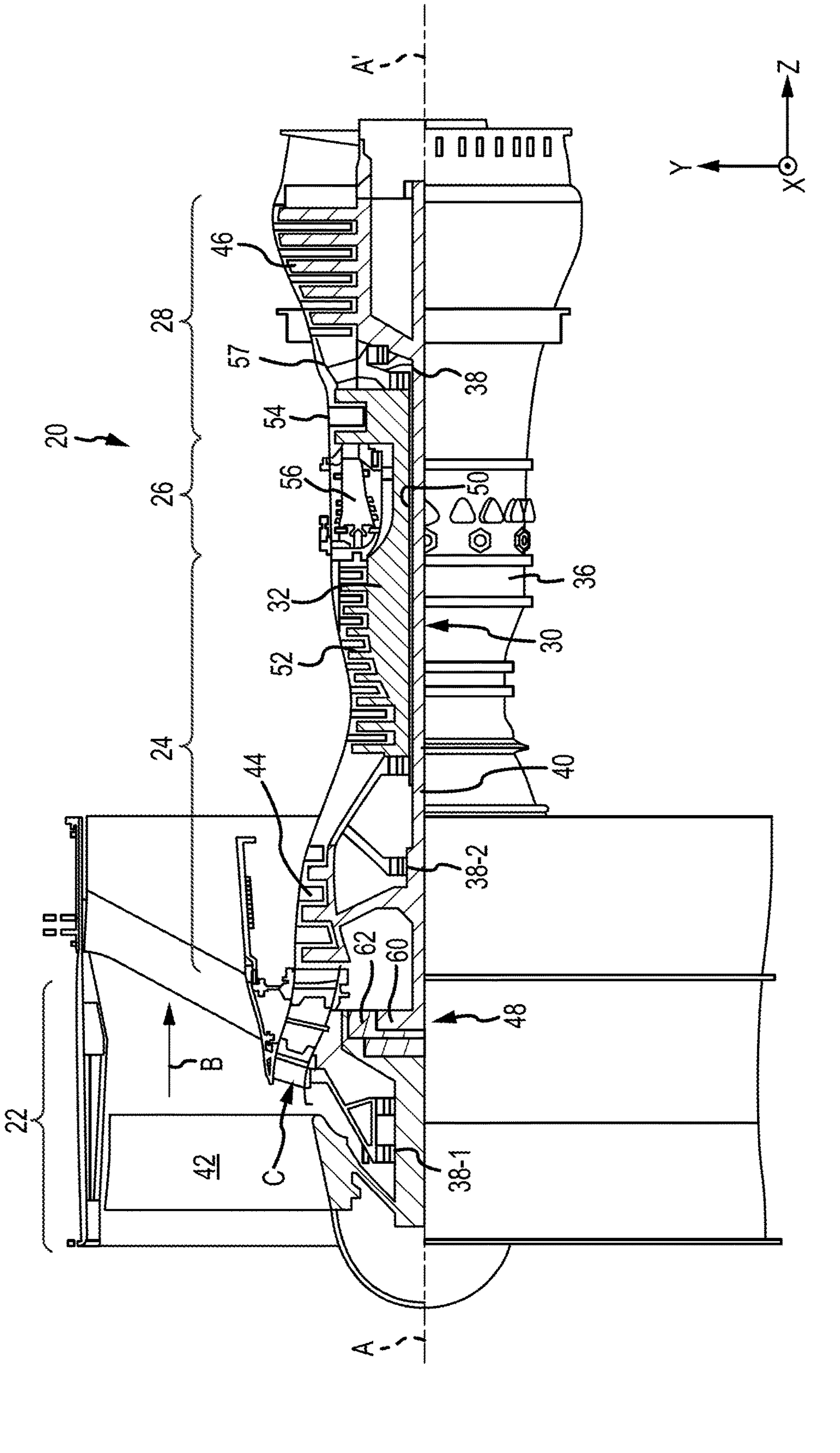
FIG. 1A illustrates a cross-sectional view of a gas-turbine engine, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Disclosed herein are systems and methods for performing localized repairs of a stator stage. The localized repairs, or rework, may, in various embodiments, address defects or damage to cast components caused from either production or in service use. Historically, such repairs may have been performed by a manual tungsten inert gas (TIG) weld processes which is labor intensive and frequently results in excessive distortion and heat input from the nature of manual weld processing. In some cases, significant rework is required covering large portions or segments of a component. Powder bed fusion (PBF) is an additive manufacturing technique which can produce features or segments of a component which can be welded into the place of missing or damage material. Joining PBF segments can be done with less heat input and time than conventional methods. In various embodiments, defect or damage mapping studies of production and in service components allows for maintenance shops to identify recurring areas of defects or damage. In various embodiments, these recurring areas can be defined into several standard segments that allow for automation of repairs using the PBF process. In various embodiments, the standard repair allows for process optimization as well as optimizing engineering requirements for acceptance (e.g., metallurgical impacts, structural impacts, aerodynamic impacts, etc.). These standard repairs enable definition of notches, lead in angles, or set aspect ratios that facilitate the PBF segment to be fit into the existing component and then joined into place. In various embodiments, defects or damage areas which do not fit into standard defined repairs may still be recovered by the manual TIG weld processes, but with much less impact to processing time, heat input, and distortion.

As used herein, "aft" refers to the direction associated with the tail (e.g., the back end) of an aircraft, or generally, to the direction of exhaust of the gas turbine. As used herein, "forward" refers to the direction associated with the nose (e.g., the front end) of an aircraft, or generally, to the direction of flight or motion.

Referring now to FIG. 1A, a gas turbine engine 20 is illustrated, in accordance with various embodiments. Gas turbine engine 20 may be a two-spool turbofan that generally incorporates a fan section 22, a compressor section 24, a combustor section 26, and a turbine section 28. In operation, fan section 22 can drive air along a path of bypass airflow B while compressor section 24 can drive air along a core flow path C for compression and communication into combustor section 26 then expansion through turbine section 28. Although depicted as a turbofan gas turbine engine 20 herein, it should be understood that the concepts described herein are not limited to use with turbofans as the teachings may be applied to other types of turbine engines including three-spool architectures, single spool architecture or the like.

Gas turbine engine 20 may generally comprise a low speed spool 30 and a high speed spool 32 mounted for rotation about an engine central longitudinal axis A-A' relative to an engine static structure 36 or engine case via several bearing systems 38, 38-1, etc. Engine central longitudinal axis A-A' is oriented in the Z direction on the provided X-Y-Z axes. It should be understood that various bearing systems 38 at various locations may alternatively or additionally be provided, including for example, bearing system 38, bearing system 38-1, etc.

Low speed spool 30 may generally comprise an inner shaft 40 that interconnects a fan 42, a low pressure compressor 44 and a low pressure turbine 46. Inner shaft 40 may be connected to fan 42 through a geared architecture 48 that can drive fan 42 at a lower speed than low speed spool 30. Geared architecture 48 may comprise a gear assembly 60 enclosed within a gear housing 62. Gear assembly 60 couples inner shaft 40 to a rotating fan structure. High speed spool 32 may comprise an outer shaft 50 that interconnects a high pressure compressor 52 and high pressure turbine 54. A combustor 56 may be located between high pressure compressor 52 and high pressure turbine 54. A mid-turbine frame 57 of engine static structure 36 may be located generally between high pressure turbine 54 and low pressure turbine 46. Mid-turbine frame 57 may support one or more bearing systems 38 in turbine section 28. Inner shaft 40 and outer shaft 50 may be concentric and rotate via bearing systems 38 about the engine central longitudinal axis A-A', which is collinear with their longitudinal axes. As used herein, a "high pressure" compressor or turbine experiences a higher pressure than a corresponding "low pressure" compressor or turbine.

The core airflow may be compressed by low pressure compressor 44 then high pressure compressor 52, mixed and burned with fuel in combustor 56, then expanded over high pressure turbine 54 and low pressure turbine 46. Turbines 46, 54 rotationally drive the respective low speed spool 30 and high speed spool 32 in response to the expansion.

Figure 1B:
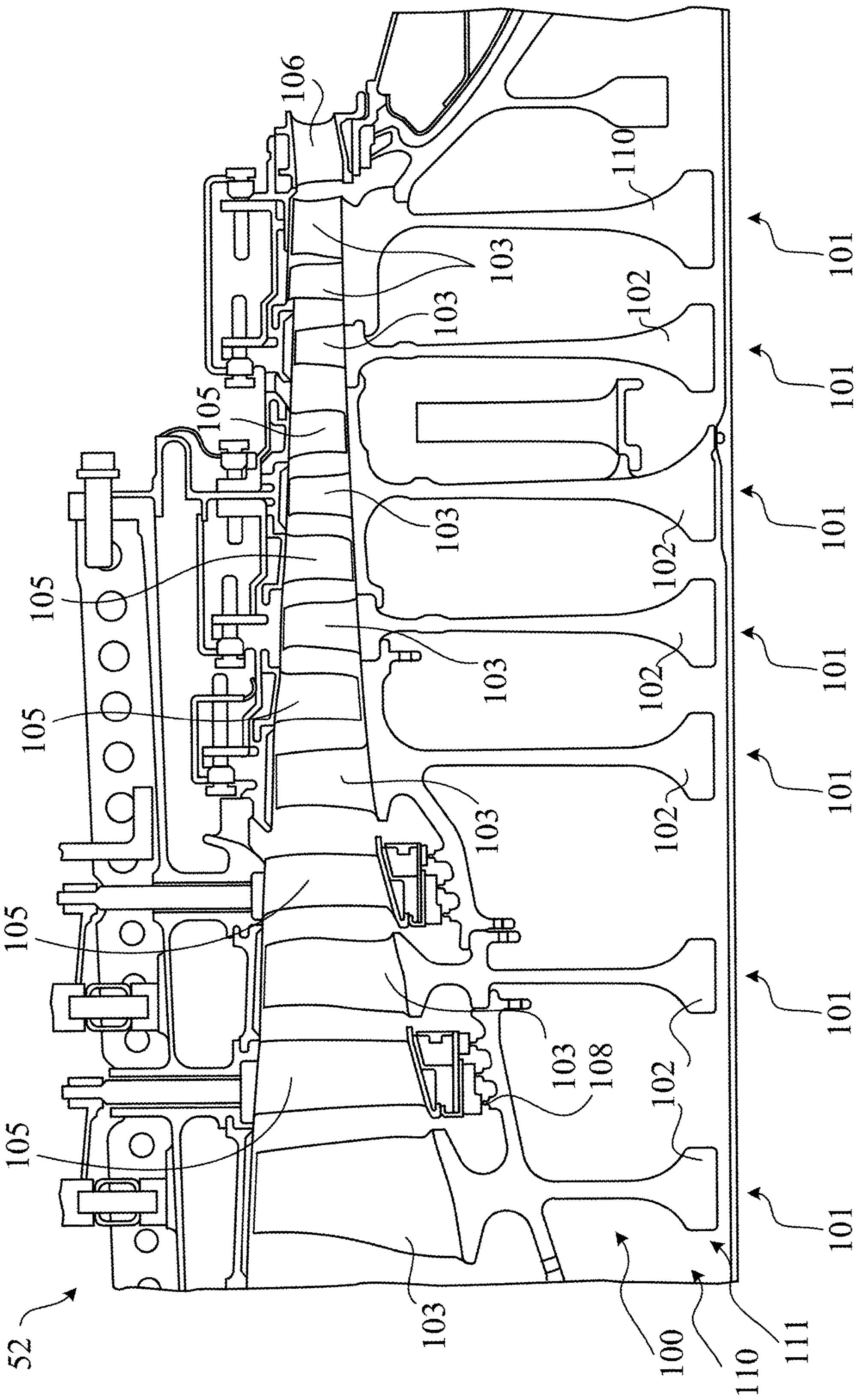
FIG. 1B illustrates a cross-sectional view of a compressor, in accordance with various embodiments.

In various embodiments, and with reference to FIG. 1B, high pressure compressor 52 of the compressor section 24 of gas turbine engine 20 is provided. High pressure compressor 52 includes a plurality of blade stages 101 (i.e., rotor stages) and a plurality of vane stages 105 (i.e., stator stages). Blade stages 101 may each include an integrally bladed rotor ("IBR") 100, such that blades 103 and rotor disks 102 are formed from a single integral component (i.e., a monolithic component formed of a single piece). Although described herein with respect to an IBR 100, the present disclosure is not limited in this regard. For example, the inspection, analysis, and repair systems disclosed herein can be utilized with bladed rotors formed of separate blades 103 and rotor disks 102 and still be within the scope of this disclosure.

Blades 103 extend radially outward from the rotor disk 102. Gas turbine engine 20 may further include an exit guide vane stage 106 that defines the aft end of high pressure compressor 52. Although illustrated with respect to high pressure compressor 52, the present disclosure is not limited in this regard. For example, low pressure compressor 44 may include a plurality of blade stages 101 and vane stages 105, each blade stage in the plurality of blade stages 101 including IBR 100 and still be within the scope of this disclosure. In various embodiments, the plurality of blade stages 101 form a stack of IBRs 110, which define, at least partially, a rotor module 111 of the high pressure compressor 52 of the gas turbine engine 20.

Figure 2:
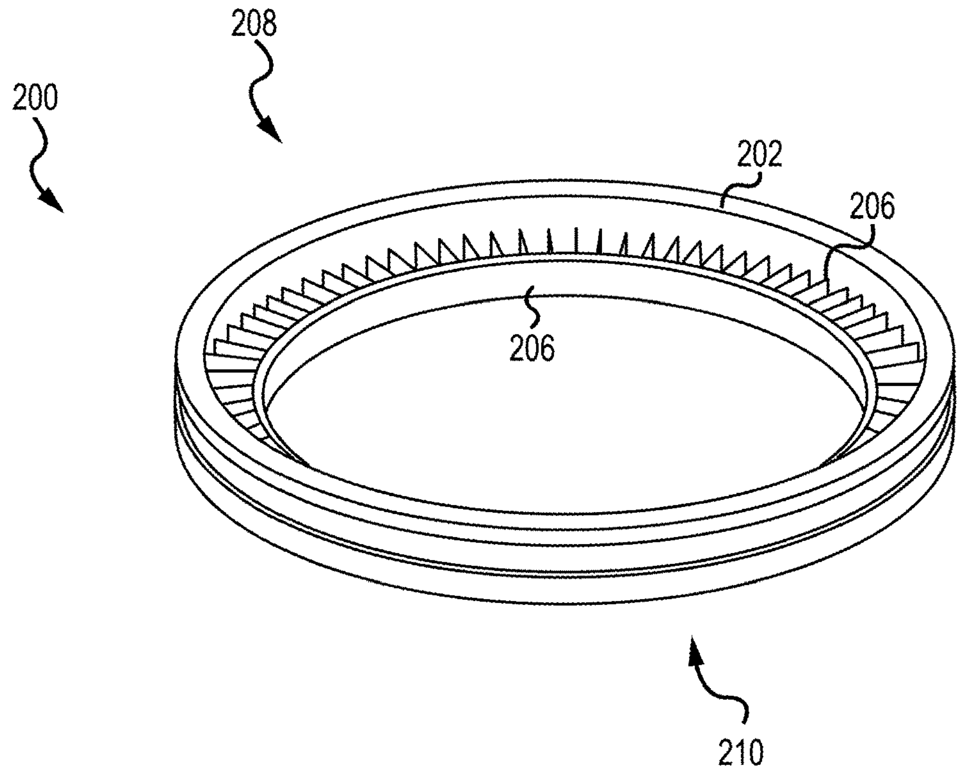
FIG. 2 illustrates a stator stage for use in a turbine engine, in accordance with various embodiments.

Referring now to FIG. 2, a stator stage 200 is illustrated, in accordance with various embodiments. In various embodiments, stator stage 200 may be one of the plurality of vane stages 105 described above in FIGS. 1A and 1B. In various embodiments, stator stage 200 may be representative of any stator stage used within a turbine engine (e.g., gas turbine engine 20). Stator stage 200 includes an outer diameter (OD) 202, an inner diameter (ID) 204, and a stator vane 206 of a plurality of stator vanes (also referred to as airfoils). Stator stage 200 has a leading edge 208 and a trailing edge 210, accordingly, each of the plurality of stator vanes (e.g., stator vane 206) has a leading edge and a trailing edge. The plurality of stator vanes (e.g., stator vane 206) extend around a circumference of ID 204 and each stator vane of the plurality of stator vanes (e.g., stator vane 206) extends from ID 204 to OD 202. Each stator vane of the plurality of stator vanes (e.g., stator vane 206) are designed and manufactured to a design specification. The design specification may be different for each stator stage 200 in a turbine engine. In various embodiments, the design specification may define a leading edge profile, a trailing edge profile, an angle with respect to OD 202, an orientation, a thickness, a curvature, and/or a position within the stator stage 200, among others.

Stator stage 200 may be manufactured as a single monolithic component using a casting process, an additive manufacturing process, or other manufacturing process. In various embodiments, one or more defects may be introduced to one or more of OD 202, ID 204, and/or one or more of the plurality of stator vanes 206. In various embodiments, the defects may be surface defects. In various embodiments, the defects may be subsurface defects.

Figure 3:
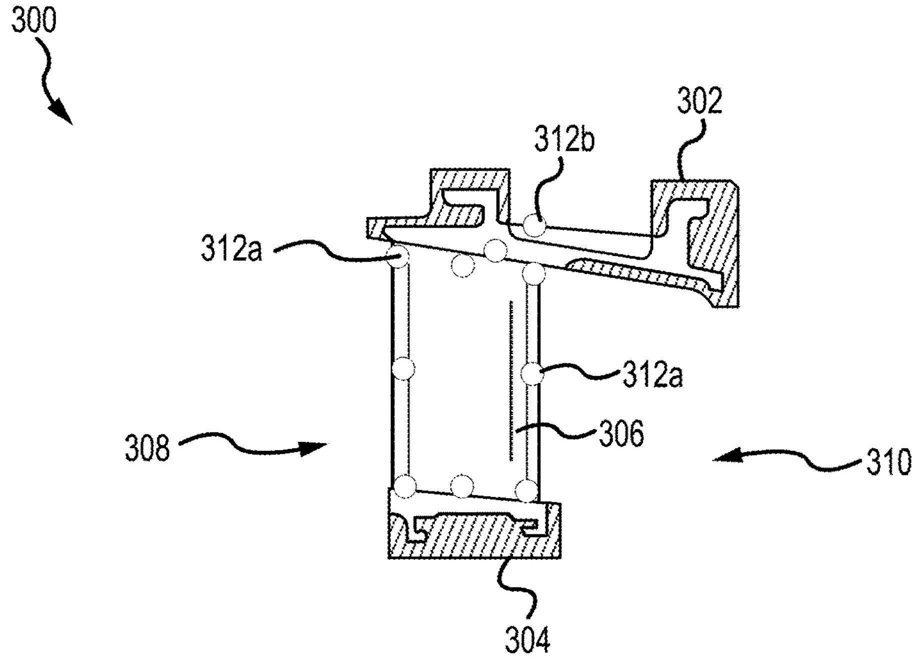
FIG. 3 illustrates a defect heat map of defects in a stator stage that is used in a turbine engine, in accordance with various embodiments.

Referring now to FIG. 3, a defect heat map 300 illustrating common defect locations in stator stage 200 and stator vanes 206, in accordance with various embodiments. Defect heat map 300 illustrates a heat map of a cross section of a stator vane 206 of stator stage 200 including OD 202, ID 204, and a stator vane 206 having leading edge 208 and trailing edge 210, Defect heat map 300 further includes a plurality of vane defects 312*a* and a plurality of OD defects 312*b*. In various embodiments, defect heat map 300 may further illustrate a plurality of ID defects. Each vane defect 312*a* and OD defect 312*b* indicates a potential location for a defect to occur during manufacture of stator stage 200. That is, stator vane 206 may include zero defects or stator vane 206 may include one or more vane defects 312*a*. Similarly, OD 202 and/or ID 204 may include zero defects or each may include one or more OD defects 312*b* or ID defects. In various embodiments, each defect (e.g., vane defect 312*a*, OD defect 312*b*, etc.) may be on the surface of stator vane 206, OD 202, or ID 204. In various embodiments, each defect (e.g., vane defect 312*a*, OD defect 312*b*, etc.) may be below the surface (i.e., subsurface) of stator vane 206, OD 202, or ID 204.

Referring now to FIGS. 4A-4D, a perspective view of a section 400 of a stator stage (e.g., stator stage 200) is illustrated, in accordance with various embodiments. While section 400 is illustrated for clarity and description purposes, it should be understood that section 400 remains integral with the stator stage (e.g., stator stage 200) as a whole. That is, the stator stage remains intact during the description of the systems and processes described below with respect to FIGS. 4A-4C. Section 400 includes an outer diameter (OD) 402, an inner diameter (ID) 404, and a plurality of stator vanes 406 including a first stator vane 406*a*.

The stator stage, including section 400, is analyzed for defects as described above. In various embodiments, the defects may be introduced during manufacturing or during operational use of section 400. In various embodiments, different systems may be used to analyze the stator stage for defects such as visual inspection, x-ray, blue light scanner, microwave, video, and/or thermal examinations, among others. In various embodiments, the defect analysis systems may be focused on locations of the stator stage identified by defect heat map 300 described above in FIG. 3. In the illustrated embodiments, multiple defects are identified in a segment 422 of section 400 on or near first stator vane 406*a*. Segment 422 is a portion of section 400 between the dashed lines and includes first stator vane 406*a*, a portion of OD 402, and a portion of ID 404.

A first defect 412*a* is identified on first stator vane 406*a* and near OD 402, a second defect 412*b* is identified on first stator vane 406*a* and near ID 404, and a third defect 412*c* is identified on first stator vane 406*a* between OD 402 and ID 404. In various embodiments, defects 412*a*, 412*b*, 412*c* may be on the surface of first stator vane 406*a*, may be below the surface of first stator vane 406*a*, on OD 402 adjacent first stator vane 406*a*, on ID 404 adjacent first stator vane 406*a*, or some combination thereof (e.g., first defect 412*a*). These defects are exemplary and used for illustrated and descriptive purposes. It should be appreciated that the defects occurring on first stator vane 406*a*, OD 402 adjacent first stator vane 406*a*, and/or ID 404 adjacent first stator vane 406*a* may be corrected by the systems and methods described herein.

In various embodiments, segment 422 may include one, two, three, or more stator vanes 406 depending on the location and size of the defects (e.g., defects 412*a*, 412*b*, 412*c*). While the illustrated segment 422 includes the portion of section 400 between the dashed lines, in various embodiments, segment 422 may be smaller. That is, in various embodiments, segment 422 may include a portion of first stator vane 406*a*, a portion of OD 402, and/or a portion of ID 404. This allows stator stage 200, and more specifically OD 402 and/or ID 404, to retain its shape (e.g., hoop shape) during repairs. In various embodiments, segment 422 may be standardized so that removal of segment 422 may be automated. That is the stator stage (e.g., stator stage 200), including section 400, may be defined by a plurality of standardized segments (e.g., segment 422). In various embodiments this simplifies the process of removing segment 422 as segment 422 is predefined and does not need to be calculated for each individual defect.

Figure 5A:
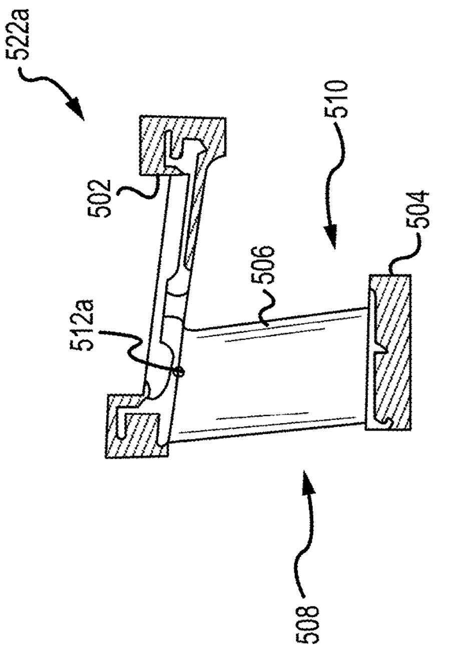
FIGS. 5A, 5B, 5C, 5D, 5E, and 5F illustrate segments of a stator stage with a defect in different locations of the segment, in accordance with various embodiments.
Figure 5B:
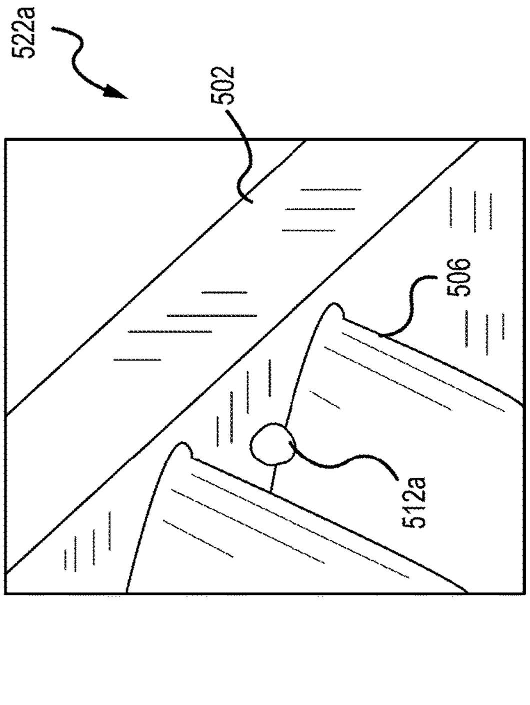
Figure 5C:
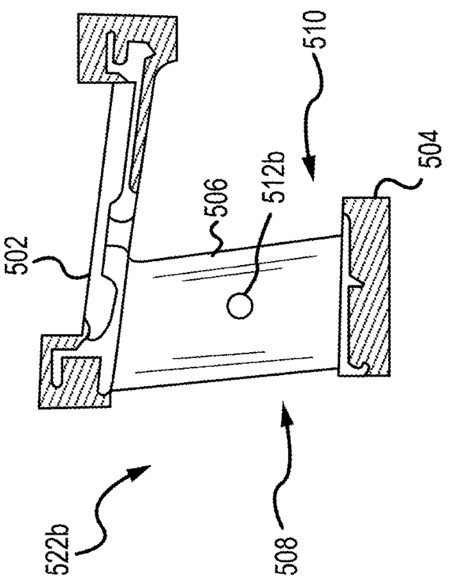
Figure 5D:
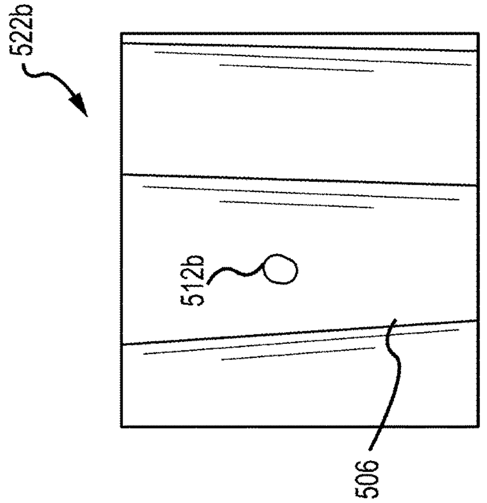
Figure 5F:
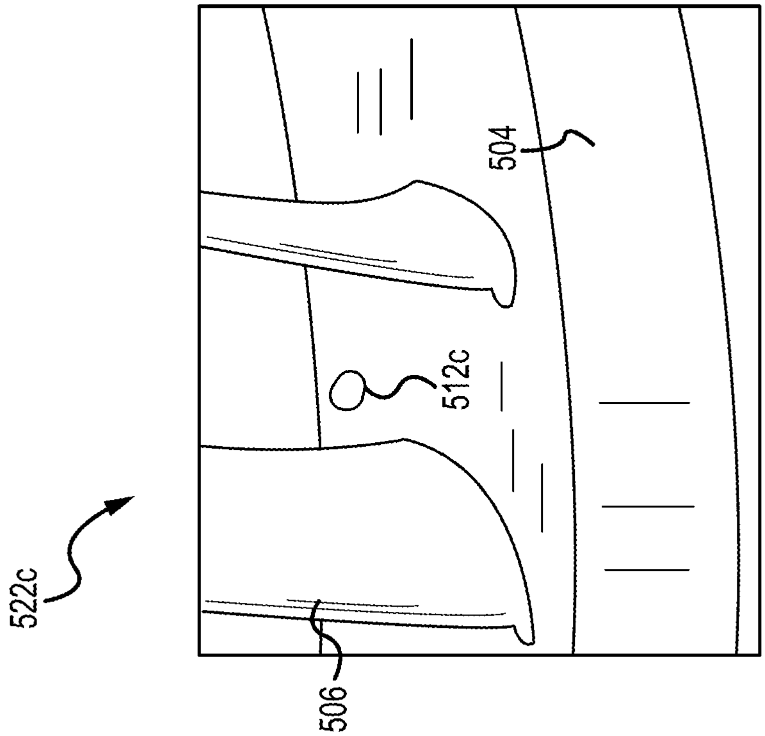
Figure 5E:
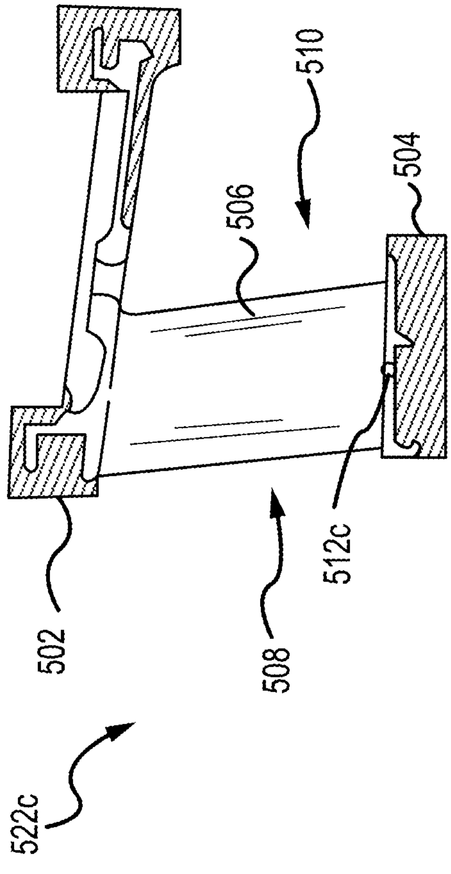

With momentary reference to FIGS. 5A-5F, a side view and a perspective view of various segments of a stator stage (e.g., stator stage 200) including defects are illustrated, in accordance with various embodiments. FIGS. 5A and 5B illustrate a first segment 522*a* including an outer an outer diameter (OD) 502, an inner diameter (ID) 504, a stator vane 506, and a first defect 512*a*. In various embodiments, first segment 522*a* may be an example of segment 422 described above in FIG. 4A. First defect 512*a* is located on OD 502. In various embodiments, first defect 512*a* may be on the surface of OD 502 or below the surface of OD 502. FIGS. 5C and 5D illustrate a second segment 522*b* including OD 502, ID 504, stator vane 506, and a second defect 512*b*. In various embodiments, second segment 522*b* may be an example of segment 422 described above in FIG. 4A. Second defect 512*b* is located on stator vane 506 between a leading edge 508 and a trailing edge 510. In various embodiments, second defect 512*b* may be on the surface of stator vane 506 or below the surface of stator vane 506. FIGS. 5E and 5F illustrate a third segment 522*c* including OD 502, ID 504, stator vane 506, and a third defect 512*c*. In various embodiments, third segment 522*c* may be an example of segment 422 described above in FIG. 4A. Third defect 512*c* is located on IND 504. In various embodiments, third defect 512*c* may be on the surface of ID 504 or below the surface of ID 504.

Figure 4A:
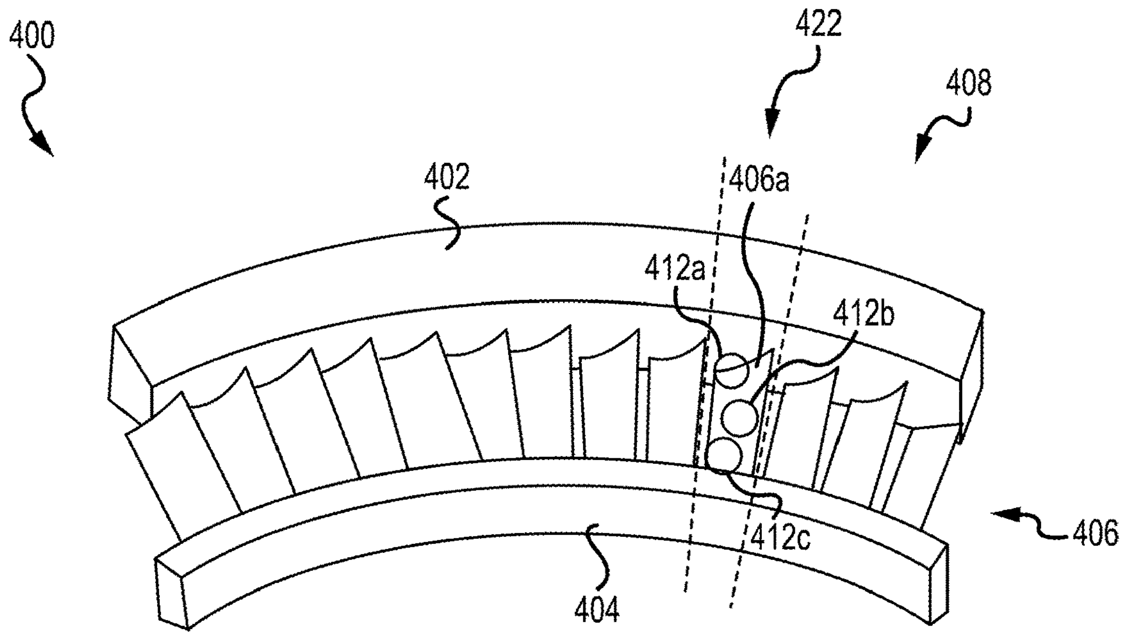
FIGS. 4A, 4B, 4C, and 4D illustrate a segment of a stator stage including a defect, removing the defect, and repairing the section of the stator stage, in accordance with various embodiments.
Figure 4B:
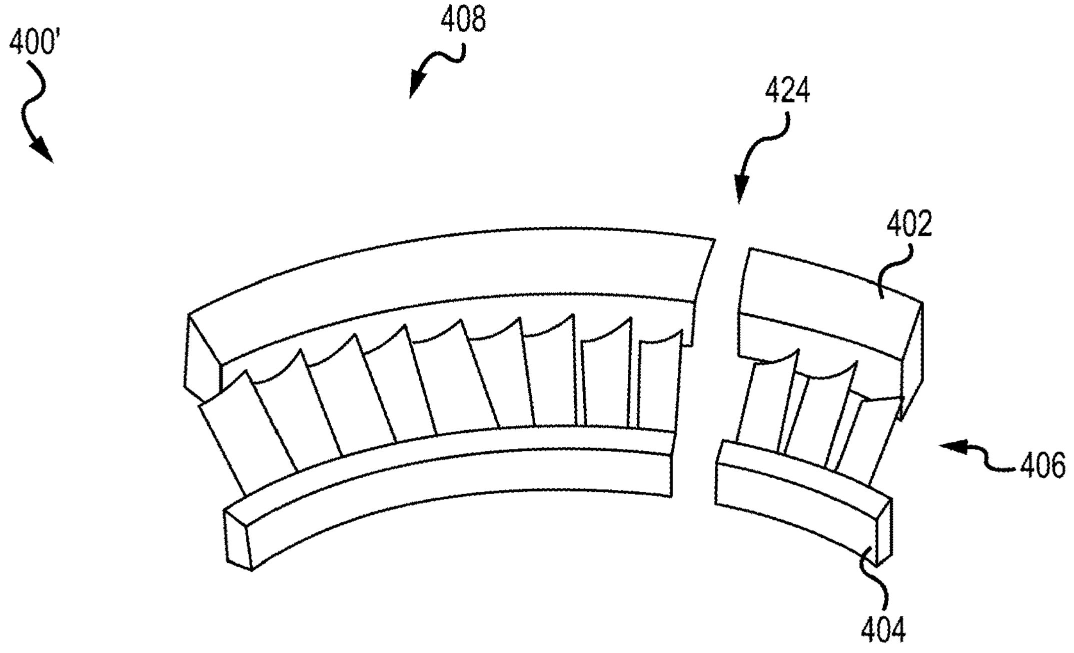

Referring now to FIG. 4B, section 400' is illustrated with segment 422 including defects 412*a*, 412*b*, 412*c* having been removed from section 400'. Removing segment 422 results in a void 424 (e.g., a gap, a space, an opening, etc.) in section 400'. Segment 422 may be removed using a grinder, a torch, a saw, a rotatory shaft tool, shears, a chisel, and/or a computer numerical control (CNC) machine, among others, to form void 424. Removing segment 422 further includes surface preparation to OD 402 and ID 404 to prepare section 400' for repair. In various embodiments, the surface preparation may include forming an edge profile on OD 402 and ID 404, such as for example, a Z-notch profile, a shiplap profile, a rabbet, a step, a bevel, or a chamfer, among others. In various embodiments, as described above, segment 422 may not include the entire OD 402 and/or ID 404. That is, void 424, in various embodiments, may result in an intact OD 402 and/or ID 404 so that stator stage 200 retains a hoop shape.

Figure 4C:
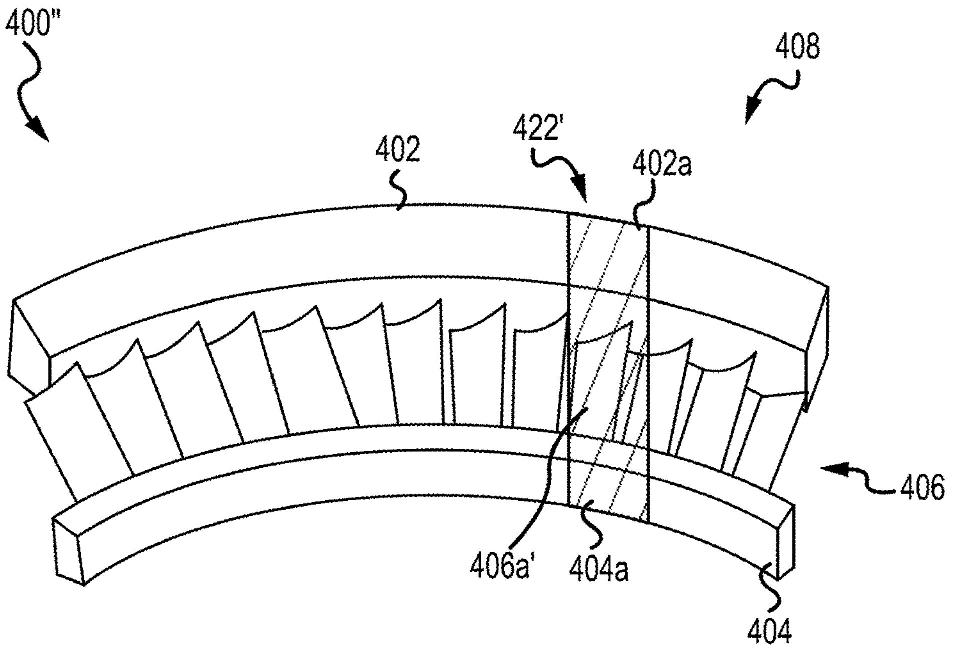

Referring now to FIG. 4C, section 400" is illustrated with a new segment 422' formed and attached to section 400", in accordance with various embodiments. In various embodiments, new segment 422' may be manufactured after removing segment 422. In various embodiments, new segment 422' may be manufactured before removing segment 422. New segment 422' includes a stator vane 406*a*', an OD portion 402*a*, and an ID portion 404*a*. In various embodiments, new segment 422' may be manufactured using a casting process. In various embodiments, new segment 422' may be from a salvaged cast segment. That is, a segment without defects that is removed from a stator stage that was previously used, that had other defects, or that was rejected for other reasons. In various embodiments, new segment 422' may be manufactured using an additive manufacturing process, such as for example, a powder bed fusion (PBF) process, a binder jetting process, a sheet lamination process, or a directed energy deposition (DED) process. The manufacturing process may produce standardized segments (e.g., new segment 422') as described above. Standardizing the segments simplifies, in various embodiments, the production of new segment 422' as unique measurements are not taken for each segment manufactured (e.g., new segment 422').

A surface treatment is then applied to new segment 422'. In various embodiments, the surface treatment may include using at least one of an abrasive flow media, a chemical removal process, a mechanical removal process, or a any combination thereof. In various embodiments, new segment 422' may be manufactured to include an edge profile on OD portion 402*a* and/or ID portion 404*a* that complements the edge profile of OD 402 and ID 404. In various embodiments, the surface treatment of new segment 422' may include forming the edge profile. The edge profile of new segment 422' allows for an improved bonding between new segment 422' and OD 402 and ID 404.

Figure 4D:
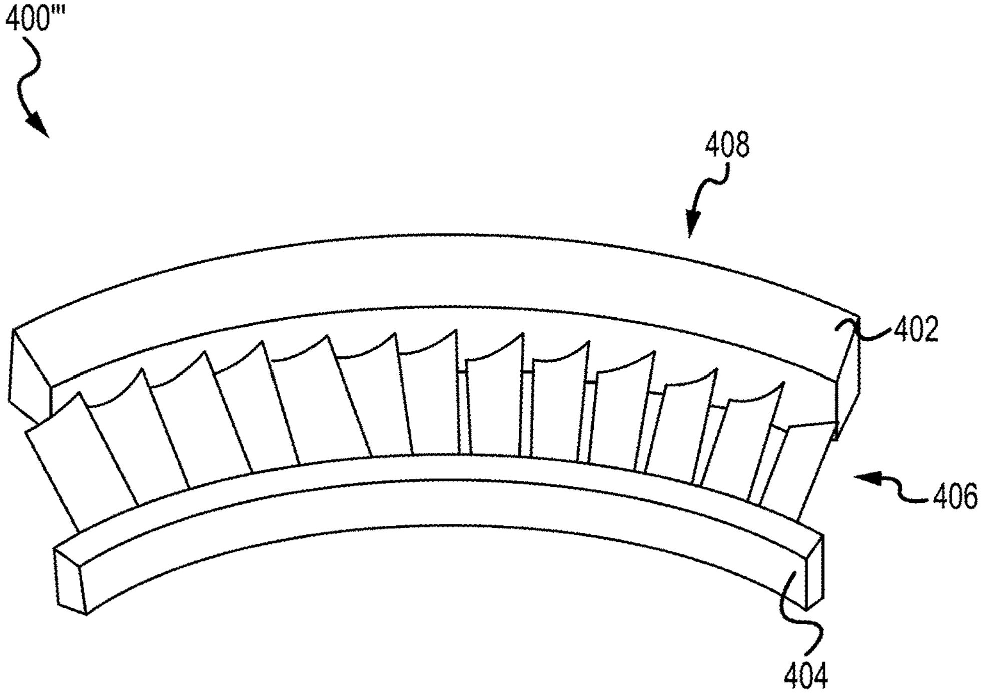

Referring now to FIG. 4D, section 400'" is illustrated with new segment 422' attached to the stator stage (e.g., stator stage 200), in accordance with various embodiments. In various embodiments, standardizing new segment 422' allows for automated attachment processes, such as welding and/or fasting processes, to be used to attach new segment 422' to section 400'". The stator stage, including section 400'" is ready to be shipped out for installation in a turbine engine, or other system. After attaching new segment 422' to section 400'", a finishing, or blending, process may be performed on the stator stage including section 400'" to shape and smooth each stator vane 406 in the stator stage. In various embodiments, the blending operation uses a material removal process, such as a milling or computer numerical control (CNC) machining smooth each stator vane of the stator stage including section 400". The blending process may further define a blend profile for each stator vane.

Figure 6:
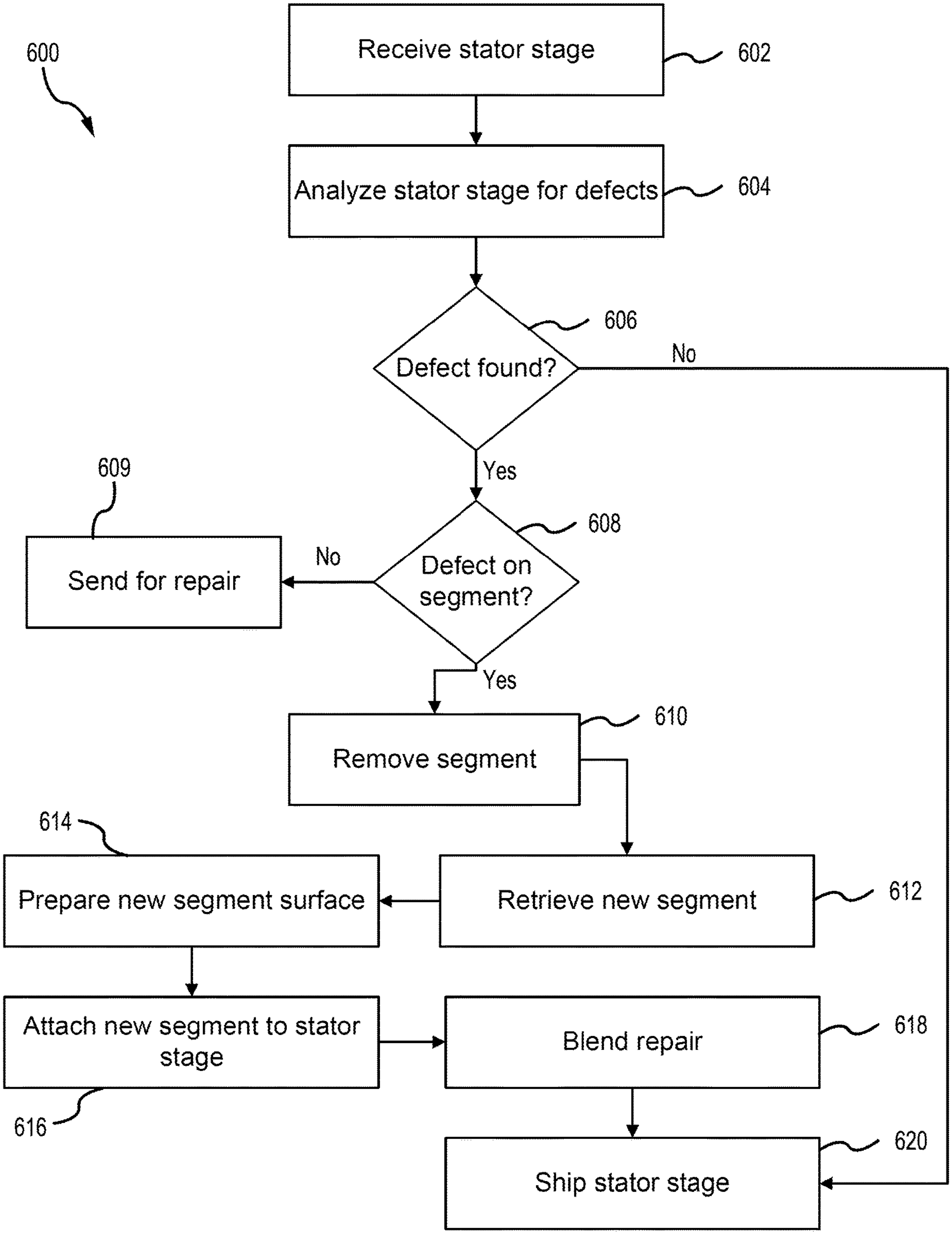
FIG. 6 illustrates a flow diagram of a method for repairing defects in a stator stage, in accordance with various embodiments.

Referring now to FIG. 6, a flow diagram of a method 600 for repairing defects in a stator stage is illustrated, in accordance with various embodiments. Method 600 may be performed by one or more different systems including a system for detecting a defect, a system for removing the defect, a system for repairing the defect, and a system for blending the defect. In various embodiments, various aspects of method 600 may be automated and optimized to reduce the cost and time to repair defects in the stator stages.

At block 602, a stator stage is received. In various embodiments, the stator stage may be stator stage 200 described above in FIG. 2. In various embodiments, the stator stage may be designed for use in a turbine engine (e.g., gas turbine engine 20). At block 604, the stator stage is analyzed for defects. In various embodiments, the analysis may include one or more of x-ray, blue light scanner, microwave, video, and/or thermal examinations, among others.

At decision block 606, if no defects are found then the method 600 proceeds to block 620. If one or more defects are found, method 600 proceeds to decision block 608. At decision block 608, if the one or more defects are not on a segment of the stator stage or on a stator vane, other the leading edge or trailing edge, method 600 proceeds to block 609 where the stator stage is sent for other repairs and method 600 ends. If the one or more defects are on the full stator vane (i.e., not the leading edge or trailing edge) or on the stator segment, method 600 proceeds to block 610.

At block 610, the segment including one or more defects is removed from the stator stage. In various embodiments, the segment may include one or more stator vanes, a portion of the outer diameter of the stator vane, and a portion of the inner diameter of the stator vane. In various embodiments, the segment may be removed using one or more of a grinder, a torch, a saw, a rotatory shaft tool, shears, a chisel, and/or a computer numerical control (CNC) machine, among others. In various embodiments, the segments of the stator stage may be standardized so that the segment removed is predefined. Standardizing the segments of the stator vane may, in various embodiments, improve efficiency and throughput of the repairs to the stator stage. In various embodiments, an edge profile is formed on the remaining portions of the stator stage in preparation to receive a new segment.

At block 612, a new segment is retrieved to replace the removed segment. In various embodiments, the new segment may be manufactured using a casting process. In various embodiments, the new segment may be manufactured using an additive manufacturing process, such as a powder bed fusion (PBF) process. In various embodiments, the new segment may be standardized in order to improve efficiency and throughput. That is, each segment of the stator stage may be standardized so that the new segment matches the space left in the stator stage by removal of the defective segment.

At block 614, a surface treatment process is performed on the new segment. In various embodiments, the surface treatment may include using at least one of an abrasive flow media, a chemical removal process, a mechanical removal process, or a any combination thereof. In various embodiments, the surface treatment may include forming an edge profile on the new segment that is complimentary to the edge profile on the stator vane. That is, the edge profile on the stator vane and the edge profile of the new segment are configured to be seamlessly joined together. The edge profile of new segment allows for an improved bonding between the new segment and the stator stage.

At block 616, the new segment is attached to the stator stage. In various embodiments, the new segment may be attached to the stator stage by welding, epoxy, glue, or fasteners, among others. In various embodiments, the attachment process (e.g., welding) may be automated because the segment and new segment are standardized and/or predefined allowing a machine to perform the attachment operation.

At block 618, the stator stage, including the new segment, is blended, or finished, to complete the repair process. The blending process may include smoothing and/or shaping of the new segment and all other stator vanes in stator stage. In various embodiments, the blending, or finishing, process may be performed if no defects are found to ensure proper form and shape of the stator vanes in the stator stage. At block 620, the stator stage is ready to be shipped and/or installed.

In various embodiments, one or more of the various steps of method 600 may be performed by a controller coupled to one or more systems described above. The controller may comprise one or more processors configured to implement various logical operations in response to execution of instructions, for example, instructions stored on a non-transitory, tangible, computer-readable medium. The one or more processors can be a general purpose processor, a microprocessor, a microcontroller, a digital signal processor (DSP), an application specific integrated circuit (ASIC), a field programmable gate array (FPGA) or other programmable logic device, discrete or transistor logic, discrete hardware components, or any combination thereof.

The controller may further comprise memory to store data, executable instructions, system program instructions, and/or controller instructions to implement the control logic of the controller.

System program instructions and/or controller instructions may be loaded onto a non-transitory, tangible computer-readable medium having instructions stored thereon that, in response to execution by a controller, cause the controller to perform various operations. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 5% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 5% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A method comprising:

receiving a stator stage including a plurality of stator vanes disposed between an outer diameter and an inner diameter;

analyzing the stator stage for subsurface defects of the stator stage;

determining, based on the analysis, that there is a first defect in a first segment of the stator stage, the first segment including a first portion of the outer diameter, a first portion of the inner diameter, and a first stator vane;

removing the first segment from the stator stage forming a void in the stator stage;

manufacturing a second segment including at least one of a second portion of the outer diameter, a second portion of the inner diameter, or a second stator vane, the second segment being the same size as the first segment;

attaching the second segment to the stator stage to fill the void;

performing a blending process on the stator stage including the second segment to smooth the plurality of stator vanes including the second stator vane.

2. The method of claim 1, wherein the analysis further includes analyzing the stator stage for surface defects.

3. The method of claim 2, wherein the analysis further includes using a defect heat map to identify locations of the stator stage with a higher probability of having a defect.

4. The method of claim 1, wherein the first defect is disposed between a leading edge of the first stator vane and a trailing edge of the first stator vane, is disposed on the first portion of the outer diameter, or is disposed on the first portion of the inner diameter.

5. The method of claim 1, wherein the first segment has a first size and shape and the second segment has the first size and shape.

6. The method of claim 1, wherein the void is defined a first edge of the outer diameter and a second edge of the outer diameter and a first edge of the inner diameter and a second edge of the inner diameter.

7. The method of claim 6, wherein the attaching the second segment includes attaching the first edge of the outer diameter and the second edge of the outer diameter to the second portion of the outer diameter and attaching the first edge of the inner diameter and the second edge of the inner diameter to the second portion of the inner diameter.

8. The method of claim 1, wherein the first segment further includes a third stator vane adjacent the first stator vane.

9. The method of claim 1, wherein the manufacturing the second segment includes using an additive manufacturing process.

10. The method of claim 9, wherein the additive manufacturing process is a powder bed fusion process.

11. A method of repairing a stator stage for use with a turbine engine, comprising:

receiving the stator stage including a plurality of stator vanes disposed between an outer diameter and an inner diameter, the stator stage having a first defect identified on a first segment of the stator stage, the first segment including a first portion of the outer diameter, a first portion of the inner diameter, and a first stator vane;

removing the first segment from the stator stage forming a void in the stator stage, the void defined by a first edge of the outer diameter and an opposing second edge of the outer diameter and a first edge of the inner diameter and an opposing second edge of the inner diameter;

manufacturing a second segment including a second portion of a second outer diameter, a second portion of a second inner diameter, and a second stator vane; and attaching the second segment to the stator stage to fill the void, including attaching the second portion of the second outer diameter to the first edge of the outer diameter and the second edge of the outer diameter and attaching the second portion of the second inner diameter to the first edge of the inner diameter and the second edge of the inner diameter.

12. The method of repairing the stator stage for use with the turbine engine of claim 11, further comprising:

performing a blending process on the stator stage to smooth and shape the plurality of stator vanes, including the second stator vane of the second segment.

13. The method of repairing the stator stage for use with the turbine engine of claim 11, further comprising:

forming a first edge profile on the first edge of the outer diameter and the opposing second edge of the outer diameter;

forming a second edge profile on the first edge of the inner diameter and the opposing second edge of the inner diameter;

forming a third edge profile on the second portion of the second outer diameter of the second segment, the third edge profile complimenting the first edge profile; and forming a fourth edge profile on the second portion of the second inner diameter of the second segment, the fourth edge profile complimenting the second edge profile.

14. The method of repairing the stator stage for use with the turbine engine of claim 11, wherein the first segment and the second segment have the same size and shape.

15. The method of repairing the stator stage for use with the turbine engine of claim 14, wherein the size and shape of the first segment and the second segment are predefined.

16. The method of repairing the stator stage for use with the turbine engine of claim 11, wherein the manufacturing the second segment including using a powder bed fusion process.

17. A method of repairing a stator stage for use with a turbine engine, comprising:

receiving the stator stage including a plurality of stator vanes and a void, the plurality of stator vanes being disposed between a first outer diameter and first inner diameter and the void being defined by a first edge of the first outer diameter and an opposing second edge of the first outer diameter and a first edge of the first inner diameter and an opposing second edge of the first inner diameter;

manufacturing a first segment including a first portion of a second outer diameter, a first portion of a second inner diameter, and a first stator vane; and attaching the first segment to the stator stage to fill the void, including attaching the first portion of the second outer diameter to the first edge of the first outer diameter and the opposing second edge of the first outer diameter, and attaching the first portion of the second inner diameter to the first edge of the first inner diameter and the opposing second edge of the first inner diameter.

18. The method of repairing the stator stage for use with the turbine engine of claim 17, wherein the void has a predefined size and shape and the first segment is manufactured to match the predefined size and shape.

19. The method of repairing the stator stage for use with the turbine engine of claim 17, wherein the manufacturing the first segment includes using a powder bed fusion process.

20. The method of repairing the stator stage for use with the turbine engine of claim 17, wherein the manufacturing the first segment includes forming an edge profile on the first portion of the second outer diameter.

* * * * *